United States Patent

Aebi et al.

[11] Patent Number: 5,288,747
[45] Date of Patent: Feb. 22, 1994

[54] METHOD OF CONTROLLING OR PREVENTING PHYTOPATHOGENIC MICROORGANISM INFESTATION OF PLANTS USING PROPICONAZOLE AS A SEED DRESSING

[75] Inventors: Rudolf Aebi, Basel; Adolf Hubele, Magden; Jürg Speich, Basel, all of Switzerland

[73] Assignee: Ciba-Geigy Corporation, Ardsley, N.Y.

[21] Appl. No.: 931,756

[22] Filed: Aug. 18, 1992

Related U.S. Application Data

[60] Division of Ser. No. 742,173, Aug. 19, 1991, abandoned, which is a continuation of Ser. No. 514,894, May 29, 1990, abandoned, which is a division of Ser. No. 218,189, Jul. 13, 1988, Pat. No. 4,940,799.

[30] Foreign Application Priority Data

Jul. 20, 1987 [CH] Switzerland ............ 2746/87-6

[51] Int. Cl.⁵ .............................. A01N 43/64
[52] U.S. Cl. ................................ 514/383
[58] Field of Search ........................ 514/383

[56] References Cited

U.S. PATENT DOCUMENTS

| | | | |
|---|---|---|---|
| 3,936,470 | 2/1976 | Heeres | 260/309 |
| 4,079,062 | 3/1978 | Van Reet | 260/308 |
| 4,101,664 | 7/1978 | Heeres | 424/273 |
| 4,101,665 | 7/1978 | Heeres | 424/273 |
| 4,101,666 | 7/1978 | Heeres | 424/273 |
| 4,119,641 | 10/1978 | Heeres | 260/340 |
| 4,120,869 | 10/1978 | Heeres | 260/340 |
| 4,139,540 | 2/1979 | Heeres | 260/340 |
| 4,154,738 | 5/1979 | Heeres | 260/329 |
| 4,156,008 | 5/1979 | Heeres | 424/273 |
| 4,160,838 | 7/1979 | Van Reet | 424/269 |
| 4,181,664 | 1/1980 | Heeres | 549/60 |
| 4,209,447 | 6/1980 | Heeres | 260/349 |
| 4,602,010 | 7/1986 | Heeres | 514/184 |

FOREIGN PATENT DOCUMENTS 0015639 9/1980 European Pat. Off.
0040007 5/1983 European Pat. Off.

OTHER PUBLICATIONS

Ca 99:48850y (1983) Vogel et al.
Structure Activity of fungicidally Active Triazoles, lecture notes (1985).
Z. Naturforsch, 44c, 85–96 (1989) Ebert et al.

*Primary Examiner*—Allen J. Robinson
*Attorney, Agent, or Firm*—Edward McC. Roberts; Marla J. Mathias

[57] ABSTRACT

The 2R,4S-isomer of formula I and the 2RS,4S-diastereoisomeric mixture of formula Ia of 1-[2-(2,4-dichlorophenyl)-4-n-propyl-1,3-dioxolan-2-ylmethyl)-1H-1,2,4-triazole

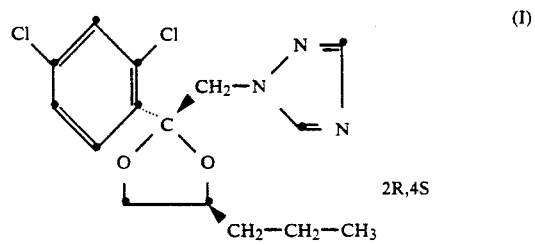

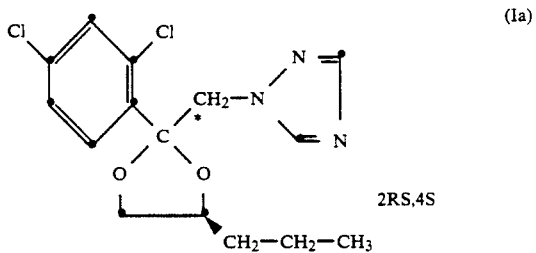

and the preparation thereof are described. The compounds of formulae I and Ia have pronounced microbicidal activity without having phytotoxic side-effects. They are used as active ingredients in microbicidal compositions, especially as seed dressings.

6 Claims, No Drawings

METHOD OF CONTROLLING OR PREVENTING PHYTOPATHOGENIC MICROORGANISM INFESTATION OF PLANTS USING PROPICONAZOLE AS A SEED DRESSING

This application is a divisional of application Ser. No. 07/742,173, filed Aug. 1, 1991, now abandoned, which is a continuation of application Ser. No. 07/514,894, filed May 29, 1990, now abandoned, which is a divisional of application Ser. No. 07/218,189, filed July 13, 1988, now U.S. Pat. No. 4,940,799, issued Jul. 10, 1990.

The present invention relates to a process for th-e preparation of the 2RS,4S-diastereoisomeric mixture of 1-[2-(2,4-dichlorophenyl)-4-n-propyl-1,3-dioxolan-2-ylmethyl]-1H-1,2,4-triazole, and to microbicidal compositions that contain those compounds as active ingredients. The invention relates also to the novel 2RS,4S-diastereoisomeric mixture and to the use of the novel compounds and of the mentioned compositions for controlling harmful microorganisms and for preventing fungus attack, especially in seed dressing.

The isomeric compounds are based on the racemic product 1-[2-(2,4-dichlorophenyl)-4-n-propyl-1,3-dioxolan-2-ylmethyl]-1H-1,2,4-triazole, known by the name "propiconazole", of the formula

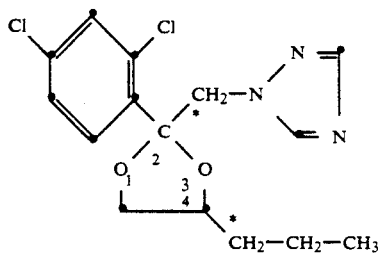

which has become known as a fungicide from GB-A-11522,657. It contains two asymmetric carbon atoms at the positions marked (*). In the preparation of this "propiconazole", approximately 60% "cis-racemate" and approximately 40 4 "trans-racemate" are formed. The "cis-racemate" contains the pair of enantiomers having the 2R,4S- and the 2S,4R-configuration, and the "trans-racemate" contains the pair of enantiomers having the 2S,4S- and the 2R,4R-configuration. GB-A-1,522,657 does not make explicit reference to this fact.

The four pure enantiomers exhibit different levels of activity as foliar fungicides and can be placed in the following order according to the degree of their activity: 2S,4R>2S,4S>2R,4S>2R,4R (E. Ebert et al., Structure Activity Relationships of Fungicidally Active Triazoles, (The Physicochemical and Biophysical Panel of the Society of Chem. Ind. 26.2.85, London)].

In recent years it has increasingly been found that the class of 1H-1,2,4-triazolyl compounds belonging to the ergosterol-biosynthesis inhibitors can be used in agrochemistry not only as plant fungicides but also as plant growth inhibitors. Examples of the many publications in which both properties are given as suggested fields of application are: EP-A-15 387, EP-A-32 200, EP-A-44 993, EP-A-53 311, EP-A-87 148, EP-A-123 160, EP-A-114 487 and EP-A-47 594. In crops of useful plants, this growth-inhibiting or growth-regulating property is very frequently undesired, since unexpected effects on plant growth may result. When used on fruit trees for controlling mildew and rust, nanism is frequently observed, for example, in the ripening fruits, and in practice that is equivalent to crop failure. At best, 1H-1,2,4-triazolyl fungicides have only slight phytotoxicity, this term being understood as meaning any form of irregular plant development. Such a side-effect is also to be observed when 1-[2(2,4-dichlorophenyl)-4-n-propyl-1,3-dioxolan-2-ylmethyl)-1H-1,2,4-triazole is used as a foliar fungicide, and especially in the case of seed dressing. Propiconazole has not been taken up as a seed dressing in practice since, even when used carefully, the germinating capacity of treated seed is generally considerably reduced and the ability of the crop to emerge is retarded too greatly.

The opinion that has formed among experts on the basis of many years' intensive research is that 1H-1,2,4-triazole derivatives in general have an effect on plant growth, generally an inhibiting effect on plant growth, that is more or less pronounced depending on the molecular structure of the particular derivative, but that is always present at least latently.

Quite unexpectedly, it has now been found that the 2R,4S-isomer of propiconazole exhibits total plant-microbicidal activity and at the same time, in contrast to the other three isomers mentioned above, has virtually no visible effects on plant growth, that is to say exhibits virtually no phytotoxicity, and that the phytotoxicity of the 2S,4S-isomer is comparatively low.

This is surprising in view of what has been said above, and all the more so since GB-A-1,522,657 gives no indication that the isomers have different biological and microbicidal or phytotoxic activities.

The object of the present invention is to provide an active ingredient that has lasting microbicidal, especially plant-fungicidal, properties without having adverse phytotoxic side-effects, and that can therefore be used especially in crops of fruit trees and as a seed dressing.

Surprisingly, it has been found that the 2R,4S-isomer of formula I of 1-(2-(2,4-dichlorophenyl)-4-n-propyl-1,3-dioxolan-2-ylmethyl]-1H-1,2,4-triazole meets these requirements fully, and that the 2RS,4S-diastereoisomeric mixture of formula Ia also satisfies these requirements in the majority of cases. This 2RS,4S-diastereoisomeric mixture is composed of equal parts of the 2R,4S-enantiomer and the 2S,4S-enantiomer and is novel, since neither the above-mentioned "locis-racemate" nor the "trans-racemate" has this isomeric composition.

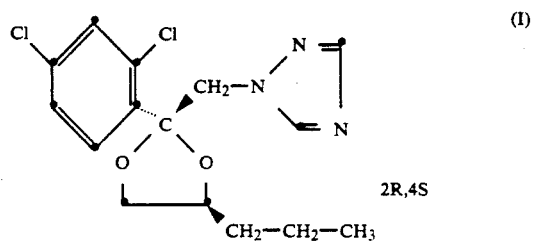

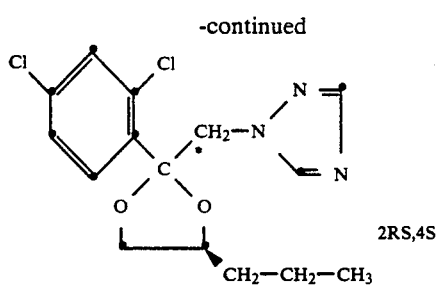

It is of decisive importance for preparative purposes that compounds having the 4S-configuration are obtained from the very beginning by the specific use of S-1,2-pentanediol of formula II

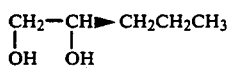

thus avoiding the formation of compounds having the 4R-configuration which, in the case of propiconazole, are mainly responsible for the phytotoxic phenomena.

The 2RS,4S-diastereoisomeric mixture of formula Ia is obtained by reaction of the diastereoisomeric mixture 2RS,4S-2-[2-(2,4-dichlorophenyl)-2-bromomethyl-4-n-propyl-1,3-dioxolane of formula III with 1,2,4-triazole of formula IV

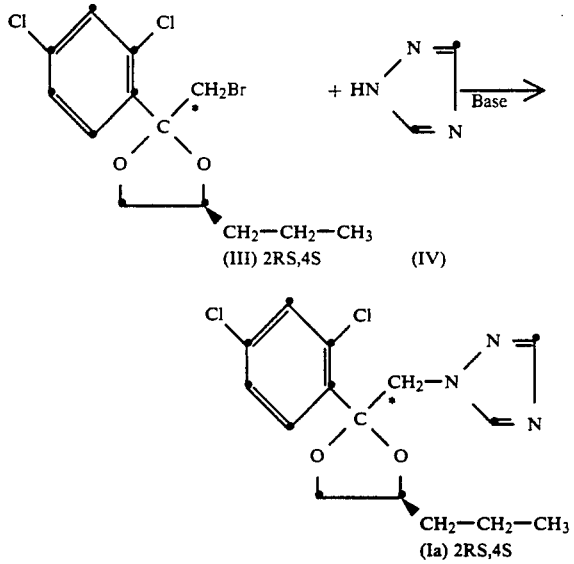

in a solvent at from 10° to 160° C., in the presence of a base as acid acceptor, to give the diastereoisomeric mixture 2RS,4S-1-[2-(2,4-dichlorophenyl)-4-n-propyl-1,3-dioxolan-2ylmethyl]-1H-1,2,4-triazole of formula Ia.

From the 2RS,4S-diastereoisomeric mixture, the 2R,4S-1-[2(2,4-dichlorophenyl)-4-n-propyl-1,3-dioxolan-2-ylmethyl]1H-1,2,4-triazole can be separated from the 2S,4S-1-[2(2,4-dichlorophenyl)-4-n-propyl-1,3-dioxolan-2-ylmethyl]-1H-1,2,4-triazole diastereoisomer and isolated. The separation can be effected by one of the customary methods on an adsorption/desorption material, for example on an acidic ion exchanger resin or on silica gel, for example by column chromatography.

The 2RS,4S-diastereoisomeric mixture or the pure 2R,4S-isomer can optionally be converted into a salt by reaction with a salt-forming acid. Examples of such acids are, of the inorganic acids, hydrohalic acids, such as hydrofluoric acid, hydrochloric acid, hydrobromic acid and hydriodic acid, and also sulfuric acid, phosphoric acid, phosphorous acid and nitric acid, and, of the organic acids, acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid and 2-acetoxybenzoic acid. This process, which is used to prepare the pure substances 2RS,4S- and 2R,4S-1-[2-(2,4-dichlorophenyl) -4-n-propyl-1,3-dioxolan-2-ylmethyl]-1H-1,2,4-triazole, is novel, and the invention relates also to this.

Solvents that may be used for the reaction of the compound of formula III with 1,2,4-triazole are—optionally halogenated—aliphatic or aromatic hydrocarbons, for example toluene, xylene, chlorobenzene, o-dichlorobenzene, methylene chloride, carbon tetrachloride and tetrachloroethylene, and aliphatic ethers, for example diethyl ether or diisopropyl ether, and also apolar, aprotic solvents, for example dimethylformamide or dimethyl sulfoxide.

Of the mentioned solvents, the apolar, aprotic solvents, especially dimethyl sulfoxide, are preferred.

Preferred bases are the alkali metal hydroxides, especially potassium hydroxide.

The preferred temperature range for the reaction is from 130° to 150° C.

As solvents or eluants for the separation by column chromatography there may be used solvents having suitable polarity, such as optionally halogenated aliphatic or aromatic hydrocarbons, esters, ethers or mixtures thereof. Preferred solvents are aliphatic hydrocarbons and aliphatic esters and mixtures thereof. Especially preferred is the ethyl acetate/hexane mixture (1:1). The separation is carried out in a temperature range of from 10° to 60° C., preferably at from room temperature to approximately 40° C.

The separation can also be carried out on other stationary phases, such as, for example, on ion exchangers having acidic radicals.

The compound of formula III can be prepared by condensation of 2',4'-dichloro-2-bromoacetophenone of formula V with S-1,2-pentanediol of formula II.

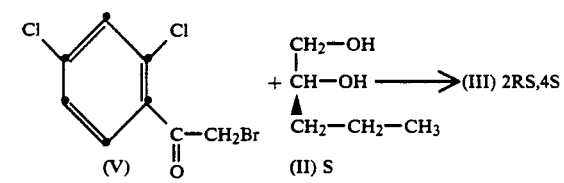

The diol of formula II is advantageously prepared by reduction of S-α-hydroxyvaleric acid of formula VI with a suitable reducing agent, such as, for example, the boranedimethyl sulfide complex of formula VII in tetrahydrofuran:

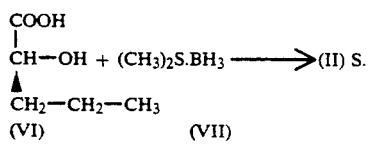

The preparation of the compound of formula VI (S) is described in J. Am. Chem. Soc. 78, 2423 (1956). It can be purified by way of suitable salts, for example by way of the S(−)-1-phenylethylammonium salt.

The compounds of formulae IV, V and VII are commercially available chemicals.

The compounds of formulae I and Ia are suitable especially for providing plants with long-term protection against attack by fungi and bacteria, and for promoting the development of the plants. As microbicidal active ingredients that are tolerated by plants, they represent a considerable enrichment of the art.

The main area in which the compounds of formulae I and Ia are used is in the control of harmful phytopathogenic fungi. Thus, the compounds of formulae I and Ia have, for practical field application purposes, a very advantageous curative, preventive and systemic action for protecting cultivated plants without having undesired side-effects on such plants. In the context of the present invention, cultivated plants are, for example, cereals (wheat, barley, rye, oats, rice); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika) or plants such as maize, tobacco, nuts, coffee, sugar cane, tea, vines, hops, bananas, avocados and natural rubber plants, as well as ornamentals.

With the compounds of formulae I and Ia it is possible to inhibit or destroy the microorganisms which occur in plants or in parts of plants (fruit, blossoms, leaves, stems, tubers, roots) in these and related crops of useful plants, while at the same time the parts of plants which grow later are also protected from such microorganisms. The compounds are effective especially against the phytopathogenic fungi belonging to the following classes: Ascomycetes (e.g. Erysiphe, Venturia, Pyrenophora (=mature form of Helminthosporium), Calonectria graminicola (=mature form of Fusarium); Basidiomycetes, e.g. Tilletia and Ustilago; Fungi imperfecti, e.g. Helminthosporium, Fusarium, Septoria, Cercospora.

The compounds of formulae I and Ia can therefore be used especially as dressing agents for protecting seeds (fruit, tubers, grains) and plant cuttings against fungus infections as well as against phytopathogenic fungi which occur in the soil. The invention also relates to seeds thus dressed.

The pathogens that are controlled are especially those which attack cereals at any stage of development, whether it be on emergence, on bushing, on ripening, on storage of the seeds (seed dressing) or on sowing. Cereal types which may be mentioned are, for example, wheat, rye, barley, oats, rice, maize and sorghum. The following important pathogens inter alia are controlled by the compound Ia and, especially, the compound I:

*Helminthosporium gramineum* (barley, wheat)
*Helminthosporium oryzae* (rice)
*Tilletia caries* (barley, wheat, rye)
*Drechslera teres* (barley, wheat)
*Ustilago tritici* (wheat)
*Ustilago maydis* (maize)
*Puccinia graminis* (wheat, barley, rye, oats)
*Erysiphe graminis* (wheat, barley, rye, oats)
*Fusarium nivale* (rye)
*Fusarium culmorum* (wheat)
*Pseudocercosporella herpotrichoides* (rye).

Only the most important crops are listed in parenthesis.

The invention thus relates also to the use of the compounds of formulae I and Ia for controlling phytopathogenic microorganisms and for preventing attack on plants such as fruit trees, the growth or fruit formation of which is customarily inhibited or otherwise adversely affected by triazole fungicides.

The invention relates especially to the use of compound Ia and especially of compound I for dressing cereal seeds, which, when treated with triazole fungicides, are usually late in emerging or generally germinate unsatisfactorily. The provision of 2R,4S-1-[2-(2,4-dichlorophenyl)-4-n-propyl-1,3-dioxolan-2-ylmethyl]-1H-1,2,4-triazole, which is tolerated fully by plants, solves the problem of protecting cereal seeds from fungicidal pathogens over the long term.

The compound of formula I or Ia is normally applied in the form of compositions and can be applied to the crop area or plant to be treated, simultaneously or in succession, with other compounds. These compounds can be fertilisers or micronutrient donors or other preparations that influence plant growth. However, they can also be selective herbicides, insecticides, fungicides, bactericides, nematicides, molluscicides or mixtures of several of these preparations, if desired together with further carriers, surfactants or application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

The compounds of formulae I and Ia are used in unmodified form or, preferably, together with the adjuvants conventionally employed in the art of formulation, and are therefore formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application are chosen in accordance with the intended objectives and the prevailing circumstances. In the agricultural sector, advantageous rates of application are normally from 50 g to 5 kg of active ingredient (a.i.) per hectare, preferably from 100 g to 2 kg a.i./ha, most preferably from 100 g to 600 g a.i./ha.

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

Particularly advantageous application-promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl glycerol or lysolecithin.

Depending on the nature of the compound of formula I or Ia to be formulated, suitable surface-active compounds are nonionic, cationic and/or anionic surfactants having good emulsifying, dispersing and wetting properties. The term "surfactants" will also be understood as comprising mixtures of surfactants.

The surfactants customarily employed in the art of formulation are described e.g. in the following publications:

"McCutcheon's Detergents and Emulsifiers Annual", BC Publishing Corp., Ringwood N.J., 1981;

Helmut Stache "Tensid-Taschenbuch", Carl Hanser Verlag, Munich/Vienna, 1981;

M. and J. Ash, "Encyclopedia of Surfactants", Vol. I-III, Chemical Publishing Co., New York, 1980-1981.

Plant-microbicidal compositions as described herein generally contain from 0.01 to 95 % active ingredient, based on propiconazole, preferably from 0.1 to 60 %, and, in addition one or more customary carriers and/or wetting agents (=surface-active compounds).

According to the present invention the compositions are characterized in that the active ingredient propiconazole contains a desirably high proportion of 2R,4S-isomer I, which is at least 45% by weight, and contains scarcely any 4R-isomers or preferably none. The greater the proportion of 2R,4S-isomer in the propiconazole component, the fewer the problems encountered when such compositions are used for application to plants, for example to apple and pear trees, but especially for seed dressing, even when too great an amount is accidentally applied. Compositions are therefore preferred in which at least 70% by weight, especially at least 90% by weight or 98 to 100% by weight, of the propiconazole component is the 2R,4S-isomer of formula I which is tolerated by plants.

If the propiconazole component is mainly the diastereoisomeric mixture 2RS,4S-1-[2-(2,4-dichlorophenyl)-4-n-propyl-1,3-dioxolan-2-ylmethyl]-1H-1,2,4-triazole, comprising equal parts of 2R,4S-isomer and of 2S,4S-isomer, then its total proportion of propiconazole is at least 90% by weight. Such an amount, which may contain 10% by weight of the phytotoxic 4R-isomer or less, will still ensure a satisfactory tolerance to plants in the majority of cases. Hence, the compositions of the invention may be admixed with small amounts of e.g. commercial (=racemic) propiconazsole such that the proportion of 4-isomer will not exceed 10% by weight, and should preferably be less than 5% by weight or, most preferably, be zero.

Whereas commercial products will preferably be formulated as concentrates, the end user will normally employ dilute formulations having concentrations of from 0.001 to 1%.

The compositions may also contain further auxiliaries such as stabilisers, antifoams, viscosity regulators, binders, tackifiers as well as fertilisers or other active ingredients for obtaining special effects.

The following Examples serve to illustrate the invention, without limiting it.

1. Preparation Examples

EXAMPLE 1

Purification of S-α-hydroxyvaleric acid

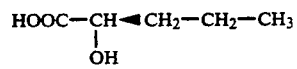

The crude acid prepared in accordance with M. Winitz et al. [J. Amer. Chem. Soc. 78, 2423 (1956)] is purified by crystallisation of its S(−)-1-phenylethylammonium salt from acetonitrile. The pure salt melts at 96°–99° C.; $[\alpha]^{20}_D = 20° \pm 1°$ (c=3.164 in methanol).

90 g (0.4 mol) of the purified salt are suspended in 1.5 litres of dioxan, and 40 ml of concentrated hydrochloric acid are added thereto. The solvent is substantially evaporated off, the viscous residue is dissolved again in 500 ml of dioxan, the S-1-phenylethylamine hydrochloride is precipitated with 2.5 litres of diethyl ether, the precipitate is filtered and then washed with diethyl ether, and the solvent is removed from the filtrate by evaporation in vacuo. 61 g of S-α-hydroxyvaleric acid are obtained in the form of a light-yellow oil which still contains approximately 20% dioxan.

EXAMPLE 2

Preparation of S-1,2-pentanediol 61 g (∼0.42 mol) of S-α-hydroxyvaleric acid, which still contains approximately 20% dioxan, are dissolved in 600 ml of tetrahydrofuran. 64 ml (0.64 mol) of borane-dimethyl sulfide complex are added dropwise to this solution at 55°–65° C. within a period of one hour, with stirring, and the mixture is heated under reflux for four hours and cooled to room temperature, and then 160 ml of methanol are added while cold. When the evolution of hydrogen has ceased, 80 ml of 0.1N hydrochloric acid are added, the mixture is stirred for ½ hour, and the solvent is evaporated off in vacuo. The partially crystalline residue is stirred with 2 litres of diethyl ether, the resulting boric acid is filtered off and the filtrate is concentrated by evaporation. The residue is dissolved in 650 ml of water, adjusted to pH 13 with barium hydroxide and filtered over silica gel, and the filtrate is concentrated to approximately 300 ml by evaporation in vacuo at 60° C. The barium borate is precipitated by the addition of 800 ml of acetone, the precipitate is filtered off, the filtration residue is washed with acetone, and the combined filtrates are concentrated by evaporation. The residue is taken up in 1.5 litres of diethyl ether, dried over sodium sulfate and filtered, and the solvent is evaporated off. Distillation of the residue yields 33 g (76% of the theoretical yield) of S-1,2-pentanediol in the form of a colourless oil, b.p. 106°–108°/21 mbar, $[\alpha]^{20}_D = -15° \pm 1°$ (c=3.028% in methanol).

EXAMPLE 3

Preparation of 2RS,4S-2- (2,4-dichlorophenyl) -2-bromomethyl-4-n-propy -1,3-dioxolane

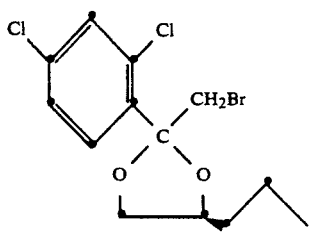

77.7 g (0.29 mol) of 21,41-dichloro-2-bromoacetophenone, 33 g (0.32 mol) of S-1,2-pentanediol and 2.5 g of p-toluenesulfonic acid in 500 ml of toluene are heated under reflux using a water separator for 16 hours. After cooling to room temperature, the mixture is diluted with 750 ml of diethyl ether, and the solution is treated with 200 ml of 1N soda solution to remove the p-toluenesulfonic acid, washed with water until neutral and dried over sodium sulfate, and the solvent is then evaporated off. Distillation of the residue yields 72.5 g (70.6% of the theoretical yield) of 2RS,4S-2-(2,4-dichlorophenyl)-2-bromomethyl-4-n-propyl-1,3-dioxolane; b.p. 125°–129°/$10^{-3}$ mbar.

EXAMPLE 4

Preparation of the diastereoisomeric mixture 2RS,4S-1-[2-(2,4-dichlorophenyl)-4-n-propyl-1,3-dioxolan-2-ylmethyl]-1H-1,2,4-triazole

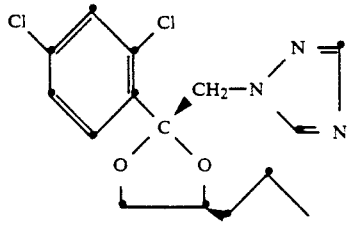

33 g (0.5 mol) of 85 KOH are added to 41.4 g (0.6 mol) of 1,2,4-triazole in 350 ml of dimethyl sulfoxide, and the mixture is stirred at 45° C. until a clear, colourless solution is formed. To this solution there are added 126 g (0.356 mol) of the diastereoisomeric mixture 2RS,4S-2-(2,4-dichlorophenyl)-2-bromomethyl-4-n-propyl-1,3-dioxolane in 50 ml of dimethyl sulfoxide, and the mixture is stirred at 140° C. for 17 hours. After cooling to room temperature, the reaction product is stirred with 1.5 litres of water and extracted with 2 litres of diethyl ether, the ether phase is washed until neutral, dried over sodium sulfate and filtered, and then the solvent is evaporated off. Distillation of the residue yields 89.3 9 (73% of the theoretical yield) of the diastereoisomeric mixture 2RS,4S-1-[2(2,4-dichlorophenyl)-4-n-propyl-1,3-dioxolan-2-ylmethyl]-1H-1,2,4-triazole; b.p. 155°–160°/$10^{-3}$ mbar.

EXAMPLE 5

Preparation of the isomer 2R,4S-1-[2-(2,4-dichlorophenyl)-4-n-propyl-1,3-dioxolan-2-ylmethyl]-1H-1,2,4-triazole The distilled product is separated into the two isomers by column chromatography over silica gel using ethyl acetate/hexane (1:1) as eluant. There are obtained 38.3 g of 2R,4S-1-[2-(2,4-dichlorophenyl)-4-n-propyl-1,3-dioxolan-2-ylmethyl]-1H-1,2,4-triazole:

$[\alpha]^{20}_D = +13° \pm 1°$ (c=4.142 * in methanol) and, as by-product, 28.4 g of 2S,4S-1-[2-(2,4-dichlorophenyl)-4-n-propyl-1,3-dioxolan-2-ylmethyl]1H-1,2,4-triazole, oil: $[\alpha]^{20}_D = -5° \pm 1°$ (c=3.17% in methanol).

2. Formulation Examples for-the active ingredients of formulae I and Ia (The figure given in parenthesis is the percentage of 2R,4S-isomer in the propiconazole active ingredient)

| 2.1. Emulsifiable concentrates | a) | b) | c) |
|---|---|---|---|
| active ingredient [70% 2R,4S] | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 30% |

Emulsions of any desired concentration can be produced from such concentrates by dilution with water. Such emulsions are suitable for foliar application or for fluid dressing.

| | a) | b) | c) | d) |
|---|---|---|---|---|
| 2.2. Solutions | | | | |
| active ingredient [90% 2R,4S] | 80% | 10% | 5% | 95% |
| ethylene glycol monomethyl ether | 20% | — | — | — |
| polyethylene glycol mol. wt. 400) | — | 70% | — | — |
| N-methyl-2-pyrrolidone | — | 20% | — | — |
| epoxidised coconut oil | — | — | 1% | 5% |
| ligroin (boiling range 160–190° C.) | — | — | 94% | — |
| 2.3. Granulates | | | | |
| active ingredient [45% 2R,4S] | 5% | 10% | | |
| kaolin | 94% | — | | |
| highly dispersed silicic acid | 1% | — | | |
| attapulgite | — | 90% | | |

The active ingredient is dissolved in methylene chloride, the solution is sprayed onto the carrier, and the solvent is subsequently evaporated off in vacuo.

| 2.4. Dusts | a) | b |
|---|---|---|
| active ingredient [98% 2R,4S] | 2% | 5% |
| highly dispersed silicic acid | 1% | 5% |
| talcum | 97% | — |
| kaolin | — | 90% |

Ready-for-use dusts are obtained by intimately mixing the carriers with the active ingredient. Such dusts are suitable for dry dressing cereal seeds.

| 2.5. Wettable powder | |
|---|---|
| active ingredient [80% 2R,4S] | 25% |
| sodium lignosulfonate | 5% |
| sodium laurylsulfate | 3% |
| sodium diisobutylnaphthalene-sulfonate | — |
| octylphenol polyethylene glycol ether (7–8 moles of ethylene oxide) | — |
| highly dispersed silicic acid | 5% |

| 2.5. Wettable powder | |
| --- | --- |
| kaolin | 62% |

The active ingredient is thoroughly mixed with the adjuvants and the mixture is ground in a suitable mill, affording wettable powders which can be diluted with water to give suspensions of the desired concentration. Such suspensions are suitable for dressing cereal seeds.

| 2.6. Emulsifiable concentrate | |
| --- | --- |
| active ingredient [70% 2R,4S] | 10% |
| octylphenol polyethylene glycol ether (4-5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Extruder granulate | |
| --- | --- |
| active ingredient [50% 2R,4S] | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.8. Coated granulate | |
| --- | --- |
| active ingredient [45% 2R,4S] | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner. If cereal seeds are added thereto in the same mixer after some time, covered, or coated, seeds are obtained in the same process.

| 2.9. Suspension concentrate | |
| --- | --- |
| active ingredient [93% 2R,4S] | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finally ground active ingredient is intimately mixed with the adjuvants, giving a suspension concentrate from which suspensions of any desired concentration can be obtained by dilution with water. Such suspensions are suitable for dressing cereal seeds (immersion dressing, spray dressing).

Wet dressing 80 g of dry cereal grains (e.g. maize) are thoroughly mixed in closable plastics beakers with 2R,4S-propiconazole of formula I or with 2RS,4S-propiconazole of formula Ia in the form of an aqueous suspension, emulsion or solution.

The substance is so applied that an active ingredient concentration of from 0.06 to 0.001%, based on the dry weight of the grains, is obtained.

3. Biological Examples

EXAMPLE 3.1

Seed dressing of wheat with stereoisomers of 1-[2-(2,4-dichlorophenyl)-4-n-propyl-1,3-dioxolan-2-ylmethyl]-1H-1,2,4-triazole and with its commercially available mixture[1], against Erysiphe graminis

[1] "Propiconazole " according to Pesticide Manual, 8th Edition, p. 10170.

Wheat seeds which are artificially infected with Erysiphe graminis are dressed with the test fungicides at a concentration of in each case 6 g active ingredient/100 kg seed (=60 ppm a.i.).

For each test fungicide, 3×100 wheat grains are placed in 3 seed trays filled with natural soil and kept in a greenhouse under the same conditions.

The effectiveness of the fungicides was calculated 30 days after sowing on the basis of the mean percentage surface area attacked by the fungus, and the delay in emergence was calculated by measuring the height of growth after 14 and after 19 days. For comparison purposes, one test was carried out using untreated, infected wheat.

After 14 and 19 days, this untreated wheat exhibited a growth height of 2.2 cm and 10.3 cm, respectively, and after 30 days it exhibited approximately 80% fungus attack.

At the same point of time, wheat seeds treated with commercially available propiconazole exhibited 1.4 cm and 8.0 cm growth height and approximately 40% fungus attack.

In contrast, the wheat seeds treated with the 2R,4S-isomer according to the invention exhibited at the same point of time a growth height of 2.1 cm and 10.3 cm and a fungus attack of less than 10%.

Likewise, the wheat seeds treated with the 2RS,4S-diastereoisomeric mixture of propiconazole according to the invention exhibited at the same point of time a growth height of 1.8 cm and 10.1 cm and a fungus attack of 10-15%.

EXAMPLE 3.2

Dressing action ag1/2against Fusarium nivale in rye

Rye which is naturally infected with Fusarium nivale is dressed on a mixer roll with the test compound, the following concentrations being used: 50 ppm a.i. (=5 g a.i./100 kg seed) and, in some cases, 100 ppm a.i.. The infected and treated rye seeds are sown in a climatic chamber in seed trays 40 cm$^2$ in size, each containing 100 seeds, and are kept under stress conditions corresponding to those of natural winter sowing at low temperatures and in the same degree of darkness as that resulting from snow cover. The seed trays are kept in complete darkness and at +4° C. for 4 weeks, and then the temperature is raised slowly to 10° C. and the alternation of day and night is simulated using artificial light.

To determine the effectiveness of the test compound, the percentage of plants attacked by Fusarium is calculated after a total of 10 weeks.

|  | No. of emerged plants | | No. of emerged plants attacked | |
|---|---|---|---|---|
|  | at 50 ppm a.i. | 100 ppm a.i. | at 50 ppm a.i. | 100 ppm a.i. |
| 2R,4S-isomer | 89 | 91 | 6 | 3 |
| 2RS,4S-diastereoisomer | 89 | — | 9 | — |
| racem. propiconazole | 80 | — | 12 | — |
| untreated and infected control | 60 | | 23 | |

— = not tested

EXAMPLE 3.3

Dressing action against Helminthosporium gramineum in barley

Winter barley of the "Cl" variety which is naturally infected with Helminthosporium gramineum is dressed on a mixer roll with the test compound at 25 ppm a.i. (=2.5 g a.i./100 kg barley).

The infected and treated barley is sown in October in the open with a seeder in plots 2 metres long and in 3 seed rows. Three replicates are carried out with each test compound.

Until evaluation is made, the test plants are cultivated under normal field conditions.

To determine the effectiveness of the test compound, the percentage of stalks attacked by Helminthosporium is assessed at the time of ear emergence.

|  | Attack | Plant growth | |
|---|---|---|---|
| 2R,4S-isomer (99%) | 0% | normal | |
| 2R,4S-isomer (70%)* | 0% | normal | 90% of seeds emerged |
| 2RS,4S-diastereoisomer | 4% | hardly affected | |
| racem. propiconazole | 11% | approx. 85% of seeds emerged | |

*(prepared by mixing 20 parts 2R,4S and 30 parts 2RS,4S)

Untreated and infected control plants exhibit 100% attack by the disease.

EXAMPLE 3.4

Dressing action against Ustilago tritici in wheat

Winter wheat which is naturally infected with Ustilago tritici is dressed on a mixer roll with the test compound at 25 ppm a.i. (=2.5 g a.i./100 kg wheat).

The infected and treated wheat is sown in October in the open with a seeder in plots 2 metres long and in 3 rows. Three replicates are carried out with each test compound.

Until evaluation is made, the test plants are cultivated under normal field conditions.

To determine the effectiveness of the compound, the percentage of ears attacked by the fungus is assessed at the time of flowering.

|  | Attack | Plant growth |
|---|---|---|
| 2R,4S-isomer | 0% | normal |
| 2RS,4S-diastereoisomer | 22% | hardly affected (approx. 95% of seeds emerged) |
| racem. propiconazole | 43% | approx. 80% of seeds emerged |

The results of the above tests 3.1 to 3.4 show that commercially available propiconazole is unsuitable for seed dressing because of its phytotoxicity, whereas the 2RS,4S-diastereoisomeric mixture produces a satisfactory protective action and the 2R,4S-isomer produces an extraordinarily high protective action, the latter compound having no effect at all on the germinating capacity of cereal seeds.

EXAMPLE 3.5

Residual protective action against Venturia inaequalis on apple shoots

Apple cuttings having 10–20 cm long fresh shoots are sprayed with a very dilute spray mixture (50 ppm active ingredient) prepared from a wettable powder of the test compound, in order give a comparative demonstration of varying degrees of growth inhibition. The treated plants are infected 24 hours later with a conidia suspension of the fungus. The plants are then incubated for 5 days at 90–100% relative humidity and are stood in a greenhouse for a further 10 days at 20°–24° C. Scab infestation is evaluated 15 days after infection.

|  | Attack | Growth inhibition (growth unaffected = 100%) |
|---|---|---|
| 2R,4S-isomer (99%) | 52% | 97% |
| 2R,4S-isomer (70%)* | 58% | 93% |
| racem. propiconazole | 77% | 80% |

*(prepared by mixing 20 parts 2R,4S and 30 parts 2RS,4S)

It is thus demonstrated that the 2R,4S-isomer and the 2RS,4S-diastereoisomer can be used in fruit growing.

What is claimed is:

1. A method of controlling or preventing infestation of cultivated plants by phytopathogenic fung, which comprises dressing the seeds from which said plants are grown with an effective amount of propiconazole having reduced toxicity to the plants relative to racemic propiconazole, said propiconazole consisting of
    a) 90 to 100 percent of the 2RS,4RS diastereomeric mixture of propiconazole, and
    b) 0 to 10 percent by weight of the 4R pr4opiconazole isomers.
2. The method of claim 1, wherein said propiconazole consists of
    a) 95 to 100 percent by weight of the 2RS,4S diastereomeric mixture, and
    b) 0 to 5 percent by weight of the 4R propiconazole isomers.
3. The method of claim 2, wherein said propiconazole comprises 0 to 1 percent of the 4R propiconazole isomers.
4. A method of controlling or preventing infestation of cultivated plants by phytopathogenic fungi, which comprises dressing the seeds from which said plants are grown with an effective amount of an active ingredient which is less toxic to the plants than racemic propiconazole, said active ingredient consisting essentially of 45 to 99 percent of 2R,4S enantiometer of propiconazole, said active ingredient further comprising less than 10 percent by weight of the 4R isomers of propiconazole.

5. The method of claim 4, which comprises dressing the seeds from which said plants are grown with an effective amount of propiconazole having reduced toxicity to the plants relative to racemic propiconazole, said propiconazole comprising 70 to 99 percent by weight of the 2R,4S enantiomer.

6. A dressed seed having reduced susceptibility to phytopathogenic fungi which is dressed with an effective amount of propiconazole having reduced toxicity to the plants relative to racemic propiconazole, said propiconazole consisting of
   a) 90 to 100 percent by weight of the 4RS,4S diastereomeric mixture of propiconazole, and
   b) 0 to 10 percent by weight of 4R propiconazole isomers and a carrier.

* * * * *